US007363087B2

(12) United States Patent
Nghiem et al.

(10) Patent No.: US 7,363,087 B2
(45) Date of Patent: Apr. 22, 2008

(54) COMPACT CONFORMAL ANTENNA FOR A MEDICAL TELEMETRY SYSTEM

(75) Inventors: David Nghiem, Shoreview, MN (US); Joshua K. Francis, East Bethel, MN (US); Paul T. Simonette, Maple Lake, MN (US); Garry L. Dublin, Maple Grove, MN (US); Randy R. Sazenski, Robbinsdale, MN (US); Gregory J. Haubrich, Champlin, MN (US); Timothy C. Aarons, Maple Grove, MN (US); Quentin S. Denzene, Andover, MN (US); Len D. Twetan, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 22 days.

(21) Appl. No.: 11/118,306

(22) Filed: Apr. 29, 2005

(65) Prior Publication Data
US 2006/0122666 A1 Jun. 8, 2006

Related U.S. Application Data

(63) Continuation of application No. 11/023,794, filed on Dec. 28, 2004, now abandoned.

(60) Provisional application No. 60/632,484, filed on Dec. 2, 2004.

(51) Int. Cl.
*A61N 1/00* (2006.01)
(52) U.S. Cl. .......................................... 607/60; 607/32
(58) Field of Classification Search .................. 607/30, 607/32, 60, 65
See application file for complete search history.

(56) References Cited

U.S. PATENT DOCUMENTS

| 4,987,424 | A | * | 1/1991 | Tamura et al. ............... 343/795 |
| 6,008,762 | A | * | 12/1999 | Nghiem ............... 343/700 MS |
| 7,047,076 | B1 | * | 5/2006 | Li et al. ........................ 607/36 |
| 2003/0222823 | A1 | * | 12/2003 | Flint et al. ................... 343/702 |

* cited by examiner

*Primary Examiner*—Carl Layno
*Assistant Examiner*—Brian T. Gedeon
(74) *Attorney, Agent, or Firm*—Ingrassia Fisher & Lorenz, P.C.

(57) ABSTRACT

A telemetry component according to an embodiment of the invention, such as a programmer or a monitor for an implantable medical device ("IMD"), includes at least one radio frequency ("RF") antenna that is configured to accommodate far-field telemetry between the telemetry component and the IMD. The RF antenna is shaped, sized, positioned, and otherwise configured to account for surface current cancellation caused by induced surface current on an electrically conductive surface of the telemetry component.

20 Claims, 8 Drawing Sheets

COMPACT CONFORMAL ANTENNA FOR A MEDICAL TELEMETRY SYSTEM

CLAIM OF PRIORITY

This application is a continuation of application Ser. No. 11/023,794, filed Dec. 28, 2004, now abandoned which claims priority from provisional application Ser. No. 60/632,484, filed Dec. 2, 2004.

TECHNICAL FIELD

The present invention relates generally to wireless communication between an implanted medical device ("IMD") and an external telemetry system, such as a programmer or monitor. More particularly, the present invention relates to antennas for use with the external telemetry system.

BACKGROUND

An IMD and an external telemetry component, such as an IMD programmer or monitor, exchange information via wireless communication techniques. For example, the telemetry component typically transmits commands to the IMD using radio frequency ("RF") data transmission methodologies. In addition, the IMD may transmit stored data or sensed physiological parameters to the external telemetry component. Traditional external telemetry components employ near-field RF data communication techniques that facilitate communication between the IMD and a telemetry head (attached to the telemetry component) that must be placed in close proximity to the IMD to establish the data communication link. Modern IMD telemetry systems leverage far-field RF data communication techniques that do not require close proximity between the IMD and the telemetry component. Indeed, such modern systems need not include a telemetry head, and the RF circuitry and RF antenna structures may be incorporated into the housing of the telemetry component itself.

The modern trend toward miniaturization of electronic equipment generally applies to IMD telemetry systems, where compact size, portability, and light weight is desirable. Indeed, a practical IMD programmer may resemble a small notebook computer having a display screen, electronic components, and computer-related hardware contained in a relatively small housing. Various packaging requirements may create physical space limitations that can impact the RF characteristics, RF specifications, or RF performance of the telemetry component.

Accordingly, it is desirable to have an IMD telemetry component, such as a programmer or monitor, that operates efficiently and effectively in a far-field mode. In addition, it is desirable to have an IMD telemetry component that incorporates an efficient and cost effective RF antenna architecture that facilitates far-field wireless communication with an IMD. Furthermore, other desirable features and characteristics of the present invention will become apparent from the subsequent detailed description and the appended claims, taken in conjunction with the accompanying drawings and the foregoing technical field and background.

BRIEF SUMMARY

An antenna arrangement configured in accordance with an embodiment of the invention is suitable for use with far-field IMD telemetry equipment. The antenna arrangement is compact in size and conformal such that it can be deployed within the limited physical space of the IMD telemetry equipment. The antenna arrangement is configured to enhance communication between the IMD and the external telemetry component. The antenna arrangement is designed in response to the surrounding IMD telemetry equipment to enhance the antenna efficiency and, therefore, the far-field performance of the telemetry system.

The above and other aspects of the invention may be carried out in one form by an RF antenna for an IMD telemetry device having electrically conducting structures. The antenna comprises a conformal radiating element shaped to minimize the detrimental effects of surface current cancellation caused by induced surface current on the electrically conducting structures.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of practical medical device telemetry systems and that the particular system described herein is merely one exemplary application for the invention.

For the sake of brevity, conventional techniques related to RF antenna design, IMD telemetry, RF data transmission, signaling, IMD operation, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description refers to features being "connected" or "coupled" together. As used herein, unless expressly stated otherwise, "connected" means that one feature is directly or indirectly connected to another feature, and not necessarily mechanically. Likewise, unless expressly stated otherwise, "coupled" means that one feature is directly or indirectly coupled to another feature, and not necessarily mechanically. Thus, although the various figures may depict example arrangements of elements, additional intervening elements, devices, features, or components may be present in an actual embodiment (assuming that the functionality of the circuit, system, or subsystem is not adversely affected).

Figure 1:
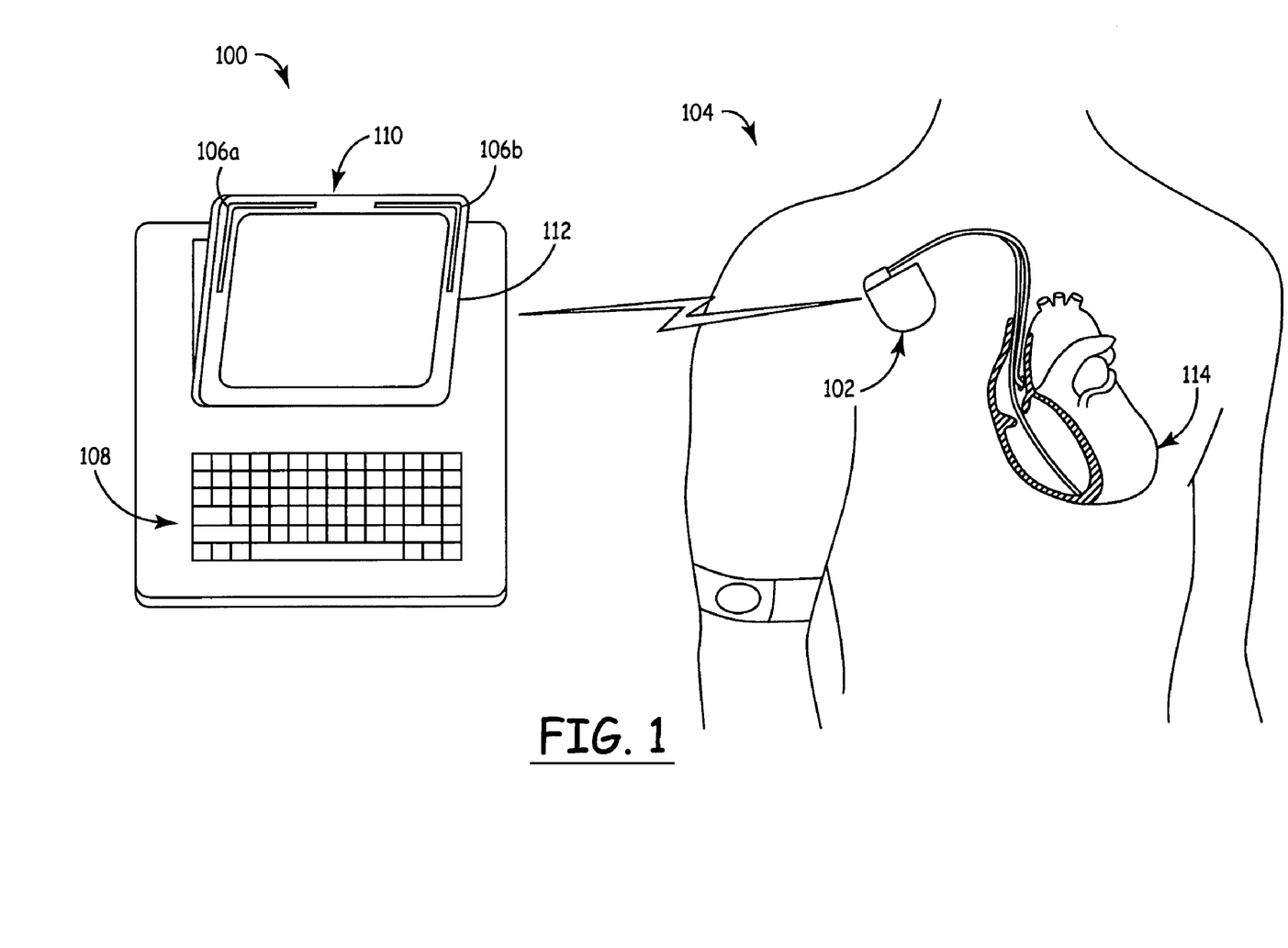
FIG. 1 is a perspective diagram showing an external telemetry device that communicates with an IMD implanted within a patient.

FIG. 1 is a perspective diagram showing an external telemetry device or component (e.g., a programmer or a monitor) 100 that communicates with an IMD 102 implanted within a patient 104. In accordance with one example embodiment of the invention, telemetry component 100 includes antennas 106a/106b arranged to provide telemetry component 100 with spatial as well as polarization diversity. Telemetry component 100 is suitably configured to transmit IMD signals, such as programming commands, to IMD 102. Telemetry component 100 is also suitably configured to receive IMD signals, such as stored operational information or physiological information, from IMD 102.

IMD 102 may be an implantable pulse generator ("IPG"), for example, a pacemaker or an implantable cardioverter-defibrillator ("ICD"). It should be appreciated, however, that telemetry component 100 may be used to communicate with any type of IMD 102. Other examples of IMD 102 include an implantable brain stimulator, an implantable gastric system stimulator, an implantable nerve stimulator, an implantable muscle stimulator, an implantable lower colon stimulator, an implantable urinary tract stimulator, an implantable drug or beneficial agent dispenser or pump, an implantable cardiac signal loop or other type of recorder or monitor, an implantable gene therapy delivery device, an implantable incontinence prevention or monitoring device, an implantable insulin pump or monitoring device, and the like.

Further, although described in terms of a programmer for purposes of illustration, the antenna configurations described herein may be used in other external devices that communicate with an IMD, such as a patient monitoring device, which need not have programming capabilities. In each case, telemetry component 100 communicates with IMD 102 to obtain IMD signals that convey IMD data such as operational information or physiological information. Depending on the type of IMD, the physiological information may include heart rate, heart rate variability, blood glucose levels, oxygen saturation, partial pressure of oxygen in the blood, blood pressure, baro-reflex measures, electrogram morphologies, lung wetness, and the like.

A user (not shown) of telemetry component 100, such as a clinician or a physician, interacts with telemetry component 100 and IMD 102 via a suitable input medium or user interface. In practice, the user interface may include a keyboard 108, a display element 110, a mouse, a touchpad, a touch screen, a trackball, or other pointing device (not shown), or the like. More specifically, telemetry component 100 provides a user interface to enable a user to provide data to telemetry component 100. Display element 110 may, for example, be a cathode ray tube ("CRT") display, a liquid crystal display ("LCD"), a light emitting diode ("LED") display, a plasma display, or the like.

Telemetry component 100 is in wireless RF communication with IMD 102. Telemetry component 100 communicates with IMD 102 by wireless transmission via antennas 106, which are configured and constructed as further described herein. Antennas 106 may be located within a housing 112 of telemetry component 100. In the example embodiment, antennas 106 are located within a portion of housing 112 that also contains display element 110. Antennas 106 are mounted within housing 112 for protection from the surrounding environment. In other words, housing 112 protects antennas 106 from incidental contact that may otherwise bend, break, or alter the RF characteristics and performance of antennas external to housing 112.

In one practical embodiment, housing 112 is fabricated from a nonconductive material such as plastic. Display element 110 may include an electrically conductive structure (or structures) such as a conductive backplane constructed of a metal, a metal alloy, or a metalized material that would otherwise be nonconductive. As described in more detail below, antennas 106 are arranged to provide spatial diversity as well as polarization diversity, in turn allowing telemetry component 100 to communicate with IMD 102 from several feet or meters away. Antennas 106 are suitably configured to achieve such far-field performance while reducing problems associated with polarization mismatches, antenna nulls, multi-path interference, and RF interference caused by other wireless devices such as cellular telephones.

In operation, telemetry component 100 interrogates IMD 102, via antennas 106, to retrieve measured data, along with currently programmed parameters and optimization target values stored by IMD 102. If IMD 102 is a pacemaker, the retrieved data includes data representing electrical activity sensed in the patient's heart 114, the output of various other sensors of IMD 102, and the rate response of IMD 102 over time. Telemetry component 100 displays some or all of these items to the user via display element 110. The user can program or reprogram IMD 102 via the user interface and input medium, e.g., keyboard 108. For example, the user may provide or adjust rate response parameters or target values of IMD 102 via the user interface and input medium, and such parameters or values are then relayed by telemetry component 100 to IMD 102 via a suitably configured transmitter/transceiver and antennas 106.

Figure 2:
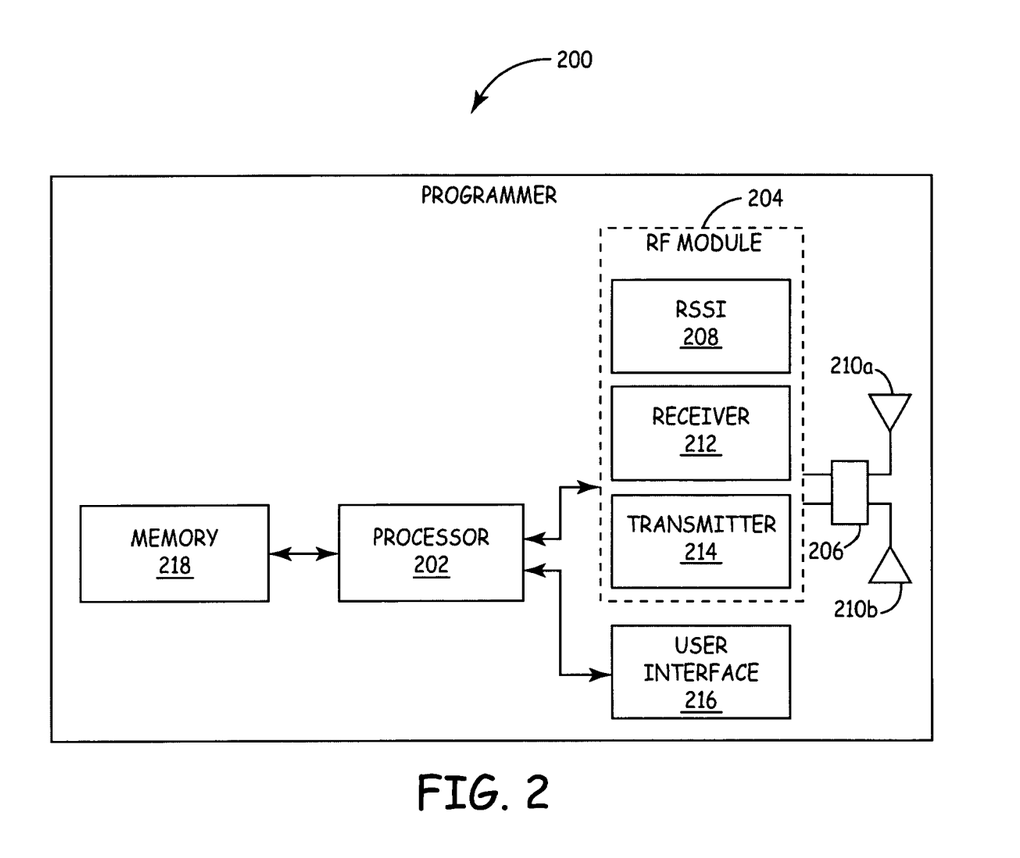
FIG. 2 is a schematic representation of an IMD telemetry component.

FIG. 2 is a schematic representation of an IMD telemetry component, such as a programmer 200. As shown in FIG. 2, programmer 200 includes a processor 202, an RF module 204, an antenna switch 206 controlled via a received signal strength indicator ("RSSI") 208, and antennas 210a/210b configured in accordance with an embodiment of the invention. Processor 202 may be any general purpose microprocessor, controller, or microcontroller that is suitably configured to control the operation of programmer 200. Programmer 200 also includes memory 218, which may be realized as any processor-readable medium, including an electronic circuit, a semiconductor memory device, a ROM, a flash memory, an erasable ROM, a floppy diskette, a CD-ROM, an optical disk, a hard disk, an organic memory element, or the like.

As mentioned above, programmer 200 communicates with an IMD using wireless data communication techniques. In a practical embodiment of the invention, programmer 200 is suitably configured to communicate with an IMD utilizing at least one data communication protocol. For example, programmer 200 may communicate with the IMD in accordance with any wireless data communication protocol.

In particular, programmer 200 is configured to transmit and receive IMD signals, via antennas 210, to and from an IMD. Antennas 210 are preferably spaced apart by approximately a half wavelength (alternatively, antennas 210 may be spaced apart by approximately a quarter wavelength) to receive IMD signals from the IMD over multiple receive paths, thus providing programmer 200 with receive diversity to reduce multi-path propagation interference as well as antenna nulls. In accordance with one practical embodiment, antennas 210 are suitably configured for an operating frequency band of approximately 402 MHz to approximately 405 MHz, and to reject frequencies of other common communication systems. With respect to diversity, antenna 210a provides a first receive path and antenna 210b provides a second receive path. Of course, more than two antennas 210 may be utilized in some embodiments for enhanced receive diversity.

Programmer 200 selects, via antenna switch 206 and RF module 204, the receive path with the strongest signal. More specifically, RF module 204 includes a receiver 212, and RSSI 208 is suitably configured to select the receive path having the strongest signal received by receiver 212. Processor 202 receives data collected by the IMD and currently programmed parameters from the IMD via receiver 212 and one of antennas 210, then processes the data in an appropriate manner. RF module 204 further includes a transmitter 214, which allows programmer 200 to program the IMD via antennas 210 (it should be appreciated that receiver 212 and transmitter 214 may be incorporated into an integrated transceiver component for RF module 204, where the transceiver includes receive circuitry and transmit circuitry). Such programming may include the programming of new parameters and/or optimization target values for the IMD. In practice, programmer 200 transmits IMD signals to the IMD using one of the antennas 210.

As discussed above, programmer 200 provides a user interface 216 by which a user of programmer 200, such as a clinician or a physician, interacts with programmer 200 and the corresponding IMD. In the example shown in FIG. 2, user interface 216 is a graphical user interface ("GUI") displayed on a suitably configured display element. A user interacts with user interface 216 via the display element and at least one input medium such as a keyboard, mouse, touch screen, or the like as described above in connection with FIG. 1.

Figure 3:
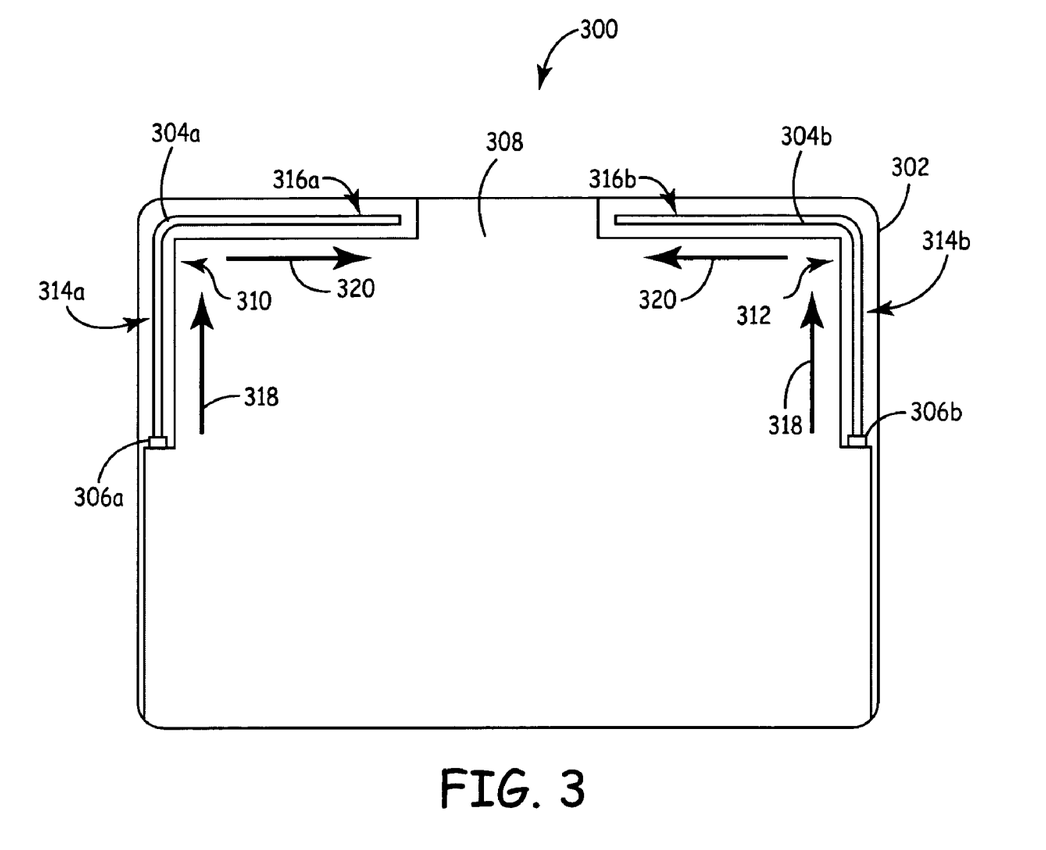
FIG. 3 is a schematic representation of a portion of an IMD telemetry component configured in accordance with an embodiment of the invention.

FIG. 3 is a schematic representation of a portion of an IMD telemetry component configured in accordance with an embodiment of the invention. In this example, FIG. 3 depicts a display element 300 of an IMD telemetry component, where a front portion of a housing 302 for the telemetry component has been removed to show the interior of display element 300. Display element 300 includes antennas 304a/304b, connectors 306a/306b for antennas 304a/304b, respectively, and a casting 308. As described above, antennas 304 are located within nonconductive housing 302 to protect antennas 304 from damage caused by the surrounding environment. In some embodiments, antennas 304 are attached to housing 302 via one or more fasteners. Housing 302 further covers casting 308 to protect casting 308 from the surrounding environment. As described above, housing 302 is preferably constructed from a nonconductive material such as plastic. In some embodiments, casting 308 is constructed of a conductive material, e.g., metal, and casting electromagnetically couples to antennas 304 to aid in tuning and impedance matching.

As illustrated in the example of FIG. 3, antennas 304 are preferably mounted proximate the top corners of display element 300 and within housing 302. Specifically, antenna 304a is located proximate a top left corner of display element 300 and antenna 304b is located proximate a top right corner of display element 300. Casting 308 has a top left corner 310 and a top right corner 312 that define at least a portion of the perimeter of casting 308. In the practical embodiment, antenna 304a is routed around the perimeter of casting 308 at corner 310, and antenna 304b is routed around the perimeter of casting 308 at corner 312. Due to the compact space limitations, antennas 304 may be located proximate electrically conducting structures within housing 302, such as casting 308, mounting tabs for display element 300, screws, bolts, or the like. Antennas 304 are substantially L-shaped to fit in the respective corners of display element 300 and to produce polarization diversity as described herein. In other words, each of the antennas 304 includes a first portion 314 having an approximately vertical orientation relative to the view shown in FIG. 3, and a second portion 316 having an approximately horizontal orientation relative to the view shown in FIG. 3. As described in more detail below, the specific shape of antennas 304 is intentionally contoured to avoid having portions of antennas 304 that are parallel with casting 308. In other words, the sections of antennas 304 that appear to run parallel with corners 310/312 in FIG. 3 are actually configured to be anti-parallel with adjacent sections of casting 308. In this regard, FIG. 3 only shows the general orientation and layout of antennas 304 relative to casting 308.

Portion 314 of antennas 304 has a first polarization and portion 316 of antennas 304 has a second polarization. More specifically, portion 314 has a vertical polarization (indicated by arrows 318), while portion 316 has a horizontal polarization (indicated by arrows 320). In this manner, antennas 304 provide programmer 300 with an opposite-sense elliptical polarization.

Antennas 304 are spaced a fraction of a wavelength, e.g., a half wavelength or a quarter wavelength, apart from one another to achieve spatial diversity, polarization diversity, and radiation diversity. This spacing is measured between the respective feed points, e.g., approximately between connectors 306 in FIG. 3. In this manner, antennas 304 receive signals from the IMD over multiple receive paths, providing programmer 300 with spatial, radiation, and polarization diversity, thereby reducing multi-path propagation interference and antenna nulls. In contrast to wands and other programmer heads that are generally placed in close proximity to the body of the patient to communicate IMD signals, the diversity arrangement of antennas 304, e.g., the spatial, radiation, and polarization diversity, enables reception of IMD signals over a longer range.

The radiating elements of antennas 304 are attached to connectors 306 in order to conductively connect antennas 304 with the RF module utilized by the telemetry component (e.g., RF module 204 shown in FIG. 2). More specifically, connectors 306 connect the radiating elements of antennas 304 with a receiver, transmitter, and/or transceiver, possibly via an RSSI element. In this manner, IMD signals received by antennas 304 can be relayed to the RF module and IMD signals from the RF module can be relayed to antennas 304 for transmission to the IMD. As described in more detail below, the specific shape of antennas 304 is preferably contoured to address surface current cancellation that may be caused by induced surface currents in casting 308.

Figure 4:
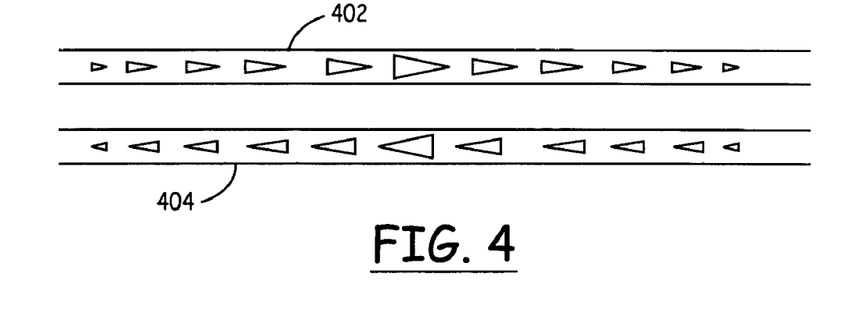
FIG. 4 is a diagram illustrating surface current cancellation in two parallel antenna radiating elements with opposite surface current.

FIG. 4 is a diagram illustrating surface current cancellation in two parallel antenna radiating elements 402/404 with opposite surface current. Opposite surface current is established by exciting the two antenna radiating elements 402/404 out of phase by 180 degrees. Excitation of antenna radiating elements 402/404 results in surface current and induced surface current; FIG. 4 depicts such an excited state. In FIG. 4, the direction of the arrows represents the direction of the surface current carried on antenna radiating elements 402/404, and the size of the arrows represents the magnitude of the surface current at that particular location. Thus, the direction of surface current in antenna radiating element 402 directly opposes the direction of surface current in antenna radiating element 404. Consequently, surface current cancellation results, and the actual surface current in either antenna radiating element 402/404 is reduced relative to the theoretical surface current in any one antenna radiating element 402/404 alone (note that if the two surface currents are in the same direction, then surface current cancellation does not occur). Simulated modeling of the arrangement shown in FIG. 4 results in an antenna efficiency (i.e., the radiated power relative to the input power) of approximately 32 percent. In contrast, the efficiency without surface current cancellation may exceed 90 percent.

Figure 5:
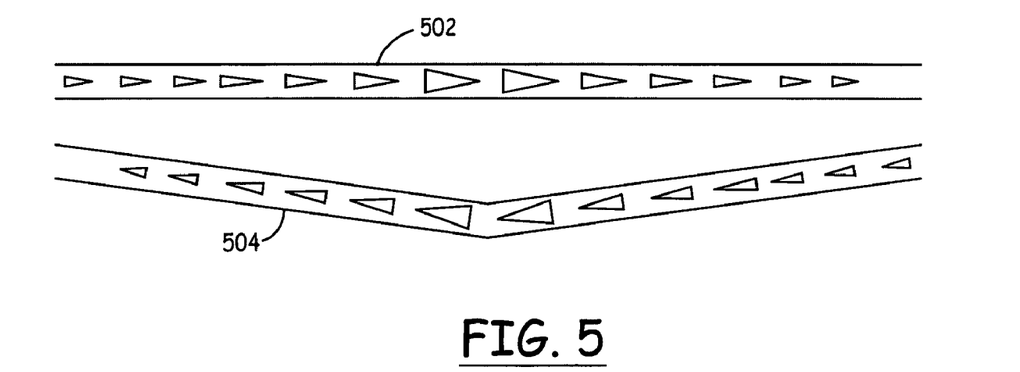
FIG. 5 is a diagram illustrating surface current cancellation in two anti-parallel antenna radiating elements with opposite surface current.

FIG. 5 is a diagram illustrating surface current cancellation in two anti-parallel antenna radiating elements 502/504 with opposite surface current. The scale for the size of the arrows in FIGS. 4 and 5 is the same. In FIG. 5, the direction of surface current in antenna radiating element 502 is the same as the direction of surface current in antenna radiating element 402. The direction of surface current in antenna radiating element 504 is generally right to left in FIG. 5. The orientation of antenna radiating element 504 relative to antenna radiating element 502, however, is anti-parallel. In other words, antenna radiating element 504 is contoured or shaped such that no portion of antenna radiating element 502 runs parallel with antenna radiating element 504. This anti-parallel arrangement reduces the amount of surface current cancellation, relative to the arrangement shown in FIG. 4. Notably, simulated modeling of the arrangement shown in FIG. 5 results in an antenna efficiency of approximately 50 percent, which represents a measurable improvement over the arrangement shown in FIG. 4.

Figure 6:
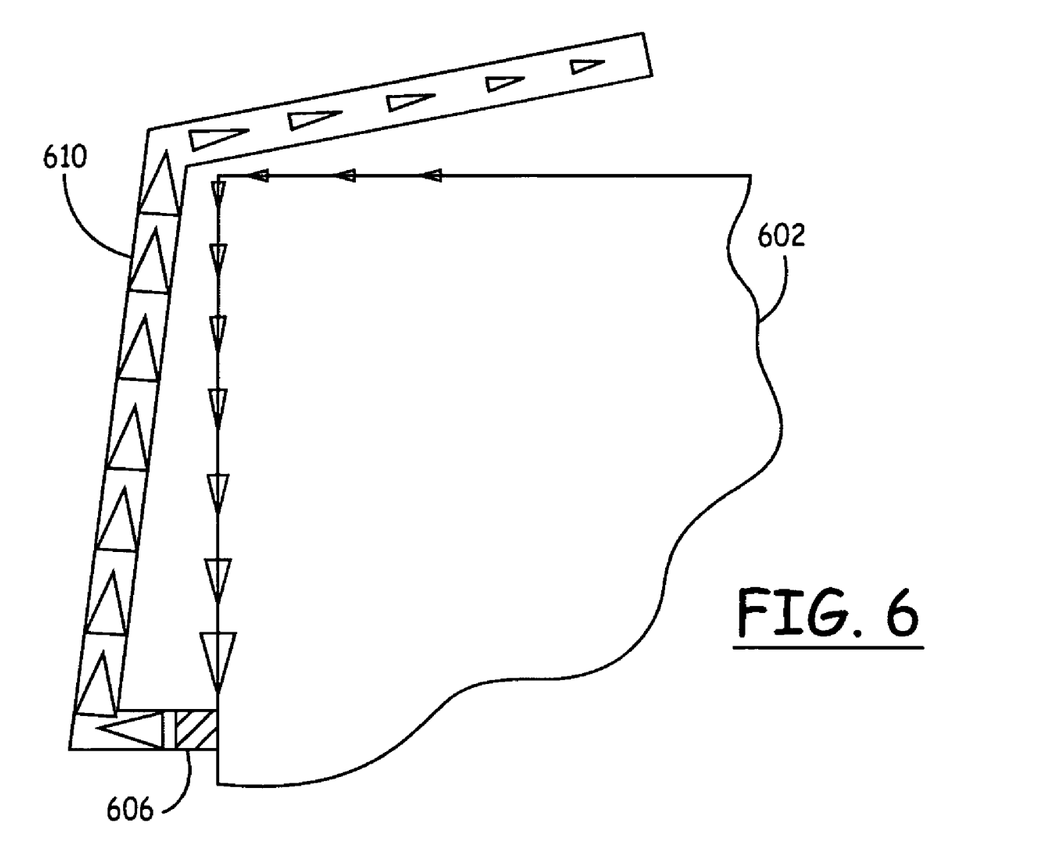
FIG. 6 is a diagram illustrating surface current cancellation in a folded monopole antenna radiating element positioned proximate to a ground plane.

The practical embodiment of the invention takes advantage of the characteristics of the anti-parallel radiating element arrangement depicted in FIG. 5 to account for surface current cancellation caused by induced surface current on the electrically conducting structure (or structures) of the telemetry component. For example, in operation, surface current may be induced on casting 308 (see FIG. 3), and such current may impact the performance of antennas 304. To address the surface current cancellation problem, antennas 304 are preferably configured to be anti-parallel to casting 308. In this regard, FIG. 6 is a diagram illustrating surface current cancellation in a folded monopole antenna radiating element 600 positioned proximate to a relatively large ground plane 602. The arrangement shown in FIG. 6 is an approximate model of the practical environment of an IMD telemetry component configured in accordance with a practical embodiment of the invention. RF power is delivered to antenna radiating element 600 via a suitable RF connector 606. The arrows on the edge of ground plane 602 represent surface current on ground plane 602 that is induced by excitation of antenna radiating element 600 (or induced by excitation of another radiating element of the telemetry component, e.g., an antenna radiating element opposite antenna radiating element 600). As shown in FIG. 6, antenna radiating element 600 is folded, bent, or contoured such that it runs anti-parallel with the adjacent sides of ground plane 602. In other words, antenna radiating element 600 forms nonzero angles with the adjacent sides of ground plane 602. This anti-parallel arrangement reduces the amount of surface current cancellation and results in more power transmitted by antenna radiating element 600 and efficient antenna operation.

Figure 7:
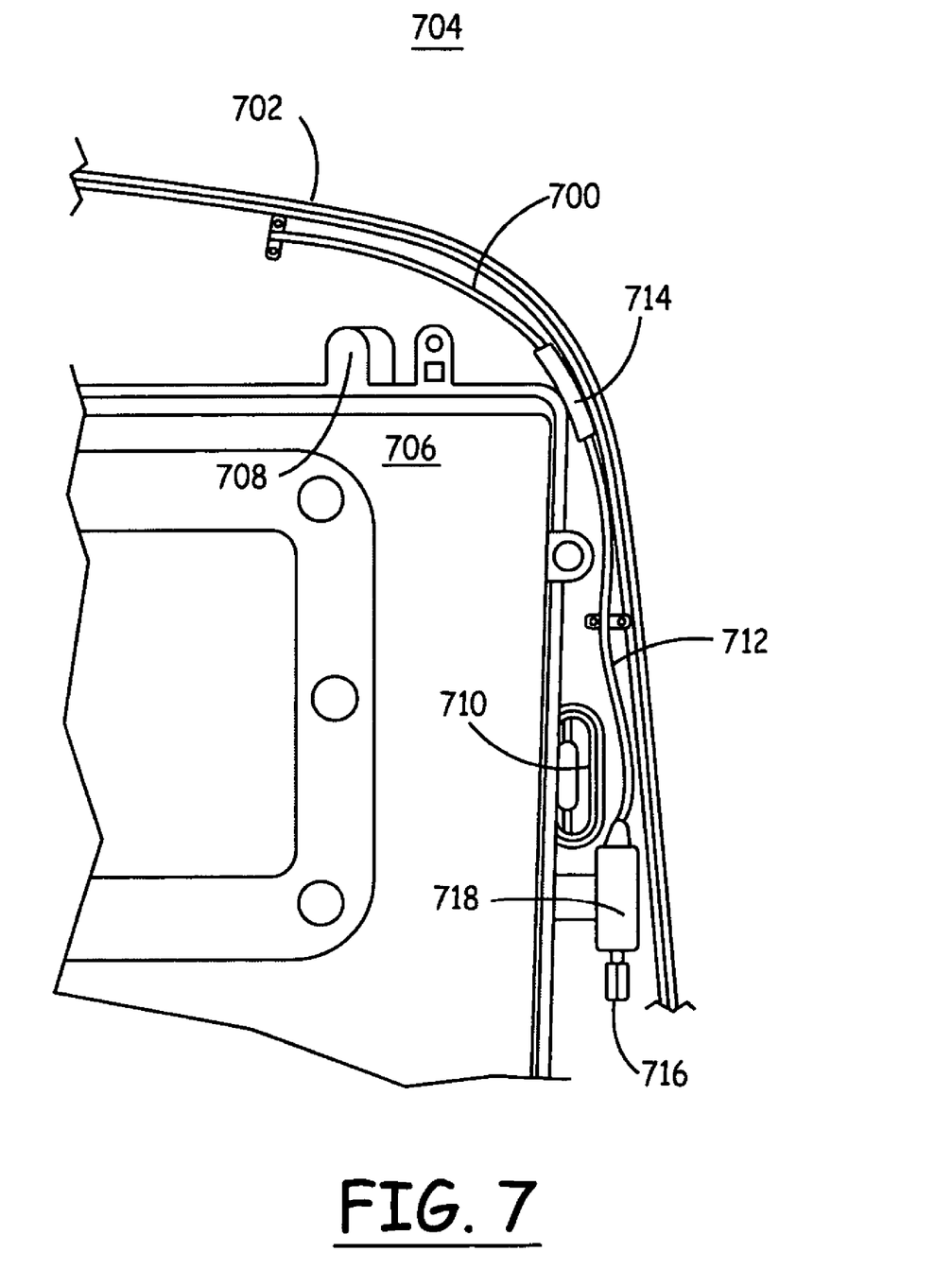
FIG. 7 is a plan view of an RF antenna located within a housing of an IMD telemetry component.

FIG. 7 is a plan view of an RF antenna 700 located within a housing 702 of an IMD telemetry component 704. RF antenna 700 is suitable for use as antennas 106 (see FIG. 1), antennas 210 (see FIG. 2), or antennas 304 (see FIG. 3), and the above description of antenna radiating element 600 also generally applies to RF antenna 700. FIG. 7 only depicts the upper right corner of a display portion of IMD telemetry component 704. As described above, the upper left corner of the display portion preferably contains a similarly configured RF antenna used for diversity purposes.

RF antenna 700 is suitably configured in accordance with one practical embodiment of the invention. As shown in FIG. 7, RF antenna 700 is positioned within housing 702 such that RF antenna 700 is biased away from electrically conducting structure 706 contained within housing 702. In other words, RF antenna 700 is positioned closer to housing 702 than to electrically conducting structure 706, and the design strives to maximize the separation between RF antenna 700 and electrically conducting structure 706 along the length of RF antenna 700. Such positioning helps to reduce the amount of induced surface current on electrically conducting structure 706 and helps to reduce the corresponding amount of surface current cancellation experienced by RF antenna 700. In the example embodiment, electrically conducting structure 706 is a metal casting configured to receive and secure a display element (not shown in FIG. 7) for IMD telemetry component 704. The metal casting may include a number of features, such as mounting tabs 708 or projections 710, that are also electrically conducting. Furthermore, the metal casting and/or housing 702 may be asymmetrical on the left and right sides.

In accordance with one practical embodiment of the invention, RF antenna 700 comprises a solid wire monopole antenna structure. For example, RF antenna 700 may include a solid copper wire 712 that serves as the radiating element. Wire 712 is preferably pliable and conformal to enable shaping as described above to account for surface current cancellation. As shown in FIG. 7, wire 712 is preferably shaped and contoured with a number of simple bends that are strategically located to minimize the length of RF antenna 700 that runs parallel to adjacent portions of electrically conducting structure 706, including mounting tabs 708, projections 710, and other conductive features. In the example embodiment, RF antenna 700 includes a nonconductive spacer 714 that is positioned and configured to insulate wire 712 from electrically conducting structure 706. Of course, a practical embodiment may employ any number of spacers 714, depending upon the space limitations, antenna topology, and shape of electrically conducting structure 706.

RF antenna 700 may include an RF connector 716 for coupling RF antenna 700 to an RF board or module (not shown) of IMD telemetry component 704. In particular, connector 716 couples RF antenna 700 to a receiver, a transmitter, and/or a transceiver of IMD telemetry component 704. In the example embodiment, RF connector 716 mates with an RF cable (not shown) coupled to the RF module of IMD telemetry component 704. The location of this RF feed point may represent a legacy design for housing 702 and, therefore, RF antenna 700 can be suitably configured for compatibility with the legacy design.

Figure 8:
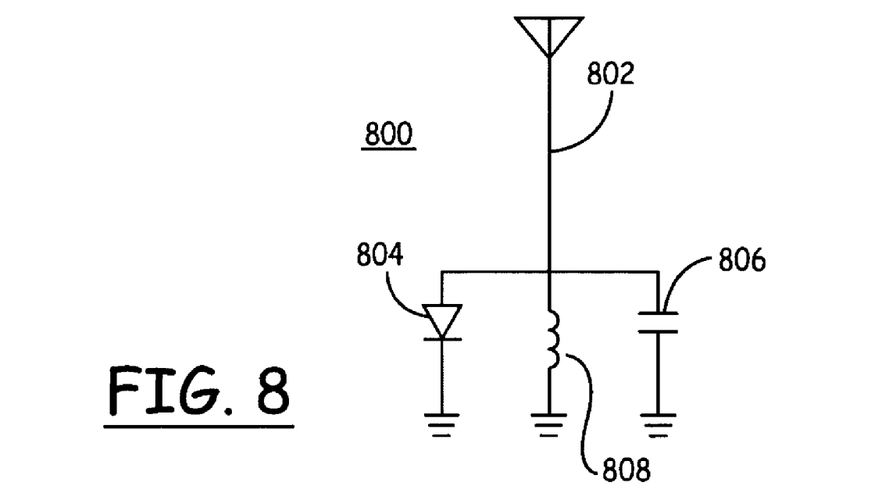
FIG. 8 is a circuit schematic of an RF antenna configured in accordance with an embodiment of the invention.

RF antenna 700 may include an element 718, located proximate RF connector 716 in the example embodiment, that includes RF matching components and an RF protection diode. Element 718 may represent an encapsulation of the RF matching components and the RF protection diode. The RF matching components facilitate impedance matching of RF antenna 700 to the RF module used by IMD telemetry component 704. The specific matching components and their topology may vary from one application to another, depending upon the desired antenna efficiency, the RF input/output impedance, the operating frequency band, the desired return loss, and other practical considerations. In this regard, FIG. 8 is a circuit schematic of an RF antenna 800 configured in accordance with one practical embodiment of the invention. RF antenna 800 includes a radiating element 802, an RF protection diode 804, a matching capacitor 806, and an optional matching inductance 808 (matching inductance 808 may not be necessary or desirable in some applications). As shown, RF protection diode 804, matching capacitor 806, and matching inductance 808 are each coupled between radiating element 802 and an RF ground potential. The use of a simple monopole wire 712 facilitates the use of a simple matching circuit for RF antenna 700 (i.e., only a shunt matching capacitor 806). In practice, the length of wire 712 is adjusted such that the desired matching circuit need only employ matching capacitor 806. Consequently, the actual length of wire 712 may vary between a quarter wavelength (the ideal theoretical length) and a half wavelength, and the actual length of wire 712 will depend upon the desired matching circuit configuration and the practical design of IMD telemetry component 704 (in particular, the configuration and RF characteristics of the components located within housing 702 of IMD telemetry component 704).

RF protection diode 804 is suitably configured to limit RF energy received by RF antenna 800 to thereby protect RF circuit components used by the IMD telemetry component. Such excess RF energy may be inadvertently received or coupled if an RF energy source, e.g., a cellular telephone, medical equipment, or the like, passes within close proximity to the IMD telemetry component. In one practical implementation, RF protection diode 804 is a PIN diode. Notably, in the example embodiment, RF protection diode 804 is incorporated into RF antenna 800 to serve as an "inline" protection means for remotely located RF circuit elements. Thus, the RF circuit board or RF module need not utilize RF protection circuitry. In lieu of RF protection diode 804, RF antenna 800 may employ other protection means, including, without limitation: one or more transistors; an RF switch; or the like.

In accordance with a practical embodiment of the invention, IMD telemetry component 704 employs RF antenna 700 in the top right corner as shown in FIG. 7, and a "mirror image" of RF antenna 700 in the top left corner (not shown). As mentioned above, the internal structure and configuration of a practical IMD telemetry component 704 may not be symmetrical. The size, shape, and topology of RF antenna 700, however, is suitably designed for compatible deployment in both sides of IMD telemetry component 704. In other words, two different RF antennas need not be manufactured for IMD telemetry component 704 and, therefore, production cost for IMD telemetry component 704 can be reduced. In practice, RF antenna 700 is suitably configured for balanced operation and to facilitate diversity associated with the two-antenna deployment. RF antenna 700 results in a bandwidth of approximately 10 MHz (recall that the desired operating frequency band is 401 MHz to 405 MHz), with an antenna efficiency of more than 30 percent.

Figure 9:
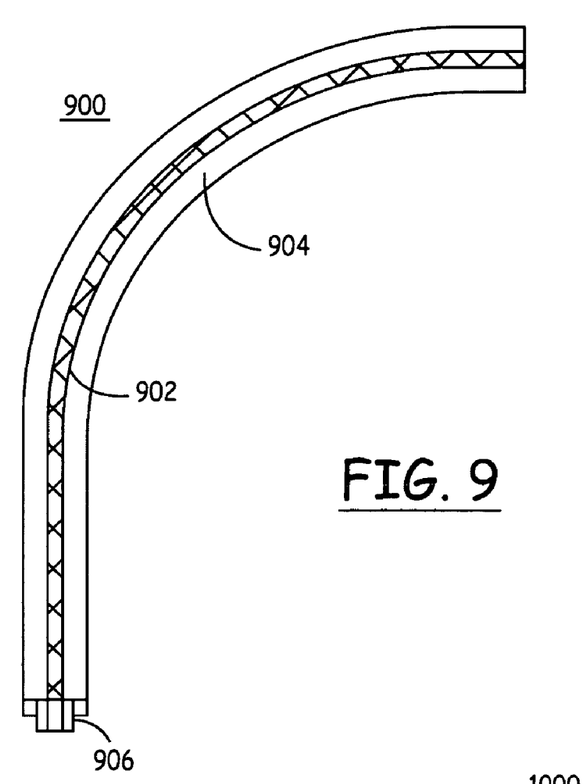
FIGS. 9-11 are schematic representations of RF antennas configured in accordance with alternate embodiments of the invention.
Figure 10:
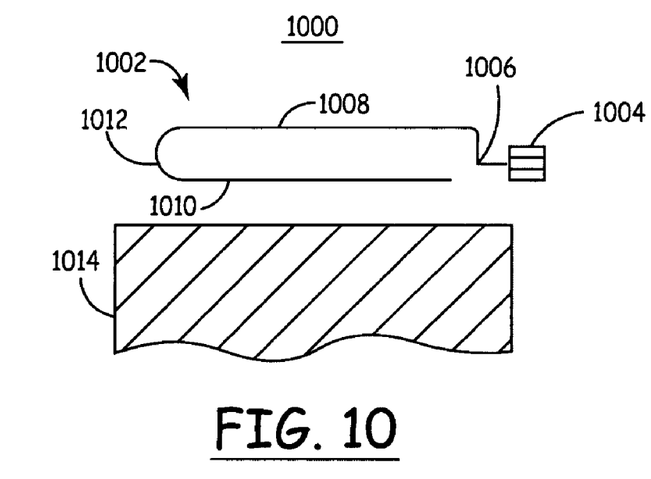
Figure 11:
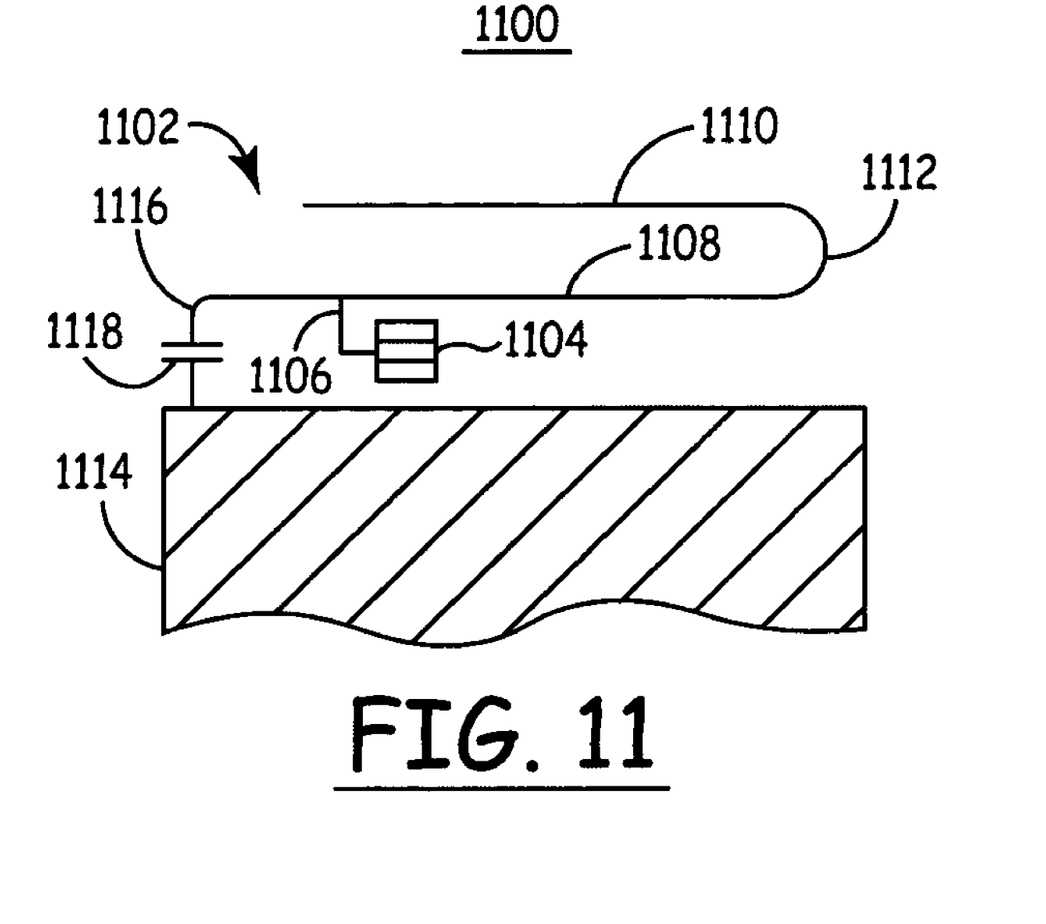

FIGS. 9-11 are schematic representations of RF antennas configured in accordance with alternate embodiments of the invention. FIG. 9 depicts an RF antenna 900 that includes a conductor 902 formed on an adhesive tape element 904. RF antenna 900 may also include an RF connector 906 coupled to the conductor 902. Although not shown in FIG. 9, RF antenna 900 may also include one or more matching elements, e.g., a surface mount capacitor. In practice, conductor 902 and adhesive tape element 904 may be flexible, thus allowing a conformal installation of RF antenna 900 within the housing of the IMD telemetry component. In particular, RF antenna 900 can be affixed or attached to the inner surface of the corners of the housing, thus maximizing the potential offset from the display element casting. RF antenna 900 is also configured as described above to account for surface current cancellation. In an alternate embodiment, in lieu of flexible adhesive tape antennas, the inner surface of the housing itself may be metalized to form RF antennas configured to account for surface current cancellation.

Although FIG. 9 depicts a simple, single conductor monopole antenna structure, alternate embodiments of the invention may utilize different RF transmission line techniques, including, without limitation: microstrip; stripline; coaxial; twin lead; coplanar waveguide; and the like.

FIG. 10 depicts an RF antenna 1000 that includes a folded monopole antenna structure 1002 and an RF connector 1004 coupled to the antenna structure 1002. Antenna structure 1002 generally includes an input section 1006, a first radiating section 1008 coupled to input section 1006, a second radiating section 1010 that runs substantially parallel to first radiating section 1008, and a bend section 1012 that couples first radiating section 1008 to second radiating section 1010. As described above in connection with other embodiments of the invention, RF antenna 1000 may be located proximate an electrically conducting structure 1014. RF antenna 1000 is preferably configured and positioned such that electrically conducting structure 1014 is located closer to second radiating section 1010 than to first radiating section 1008. This configuration reduces the amount of surface current formed on electrically conducting structure 1014, thus reducing the amount of related surface current cancellation experienced by RF antenna 1000. In this regard, a relatively high amount of surface current is carried in first radiating section 1008, while a relatively low amount of surface current is carried in second radiating section 1010. This relatively low amount of surface current results in a low amount of induced surface current on electrically conducting structure 1014. Furthermore, since most of the surface current appears on first radiating section 1008 (which is physically offset away from electrically conducting surface 1014), the overall impact of surface current cancellation is not significant.

In practice, RF antenna 1000 has a relatively wideband characteristic (approximately 60 MHz bandwidth) and RF antenna 1000 has a relatively high efficiency rating (greater than 80 percent). The high bandwidth is achievable at the cost of having a relatively large ground plane, which is established in the practical embodiment by the metal casting for the display element. As a result of the high bandwidth, RF antenna 1000 need not employ a matching circuit or any matching components. RF antenna 1000 may be implemented using a solid wire, flex tape, or metalized plastic (as described above), or in accordance with any known antenna fabrication technique. To reduce manufacturing cost, a practical embodiment may etch RF antenna 1000 onto a relatively small flex tape or other conductive element with a modestly sized ground plane. Thereafter, the small ground plane can be capacitively coupled to electrically conducting structure 1014 to create a relatively large ground plane for RF antenna 1000.

FIG. 11 depicts an RF antenna 1100 that includes a planar inverted F-shaped antenna structure 1102 and an RF connector 1104 coupled to the antenna structure 1102. Antenna structure 1102 generally includes an input section 1106, a first radiating section 1108 coupled to input section 1106, a second radiating section 1110 that runs substantially parallel to first radiating section 1108, and a bend section 1112 that couples first radiating section 1108 to second radiating section 1110. As described above in connection with other embodiments of the invention, RF antenna 1100 may be located proximate an electrically conducting structure 1114. RF antenna 1100 is preferably configured and positioned such that electrically conducting structure 1114 is located closer to first radiating section 1108 than to second radiating section 1110. Antenna structure 1102 also includes a termination section 1116 located at the end of first radiating section 1108. Thus, input section 1106 is positioned between termination section 1116 and bend section 1112. In the example embodiment, a coupling capacitor 1118 is coupled between termination section 1116 and electrically conducting structure 1114.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

What is claimed is:

1. An implanted medical device ("IMD") telemetry device comprising:
   an electrically conducting structure;
   a folded monopole antenna structure located proximate to said electrically conducting structure, said folded monopole antenna structure having an input section, a first radiating section coupled to said input section, a second radiating section parallel to said first radiating section, and a bend section coupling said first radiating section to said second radiating section, said electrically conducting structure being located closer to said second radiating section than to said first radiating section; and
   a receiver coupled to said folded monopole antenna structure, said receiver being configured to receive IMD signals via said folded monopole antenna structure, said folded monopole antenna structure being configured to account for surface current cancellation caused by induced surface current on said electrically conducting structure.

2. An IMD telemetry device according to claim 1, further comprising a transmitter coupled to said folded monopole antenna structure, said transmitter being configured to transmit IMD signals via said folded monopole antenna structure.

3. An IMD telemetry device according to claim 1, further comprising a housing containing said electrically conducting structure and said folded monopole antenna structure.

4. An IMD telemetry device according to claim 3, wherein the position of said folded monopole antenna structure is biased away from said electrically conducting structure.

5. An IMD telemetry device according to claim 3, wherein said folded monopole antenna structure comprises a conductor attached to said housing.

6. An IMD telemetry device according to claim 5, wherein said conductor is formed on an adhesive tape, and said adhesive tape is attached to said housing.

7. An IMD telemetry device according to claim 1, wherein the operating frequency band of said folded monopole antenna structure is approximately 401-405 MHz.

8. An IMD telemetry device according to claim 1, wherein said folded monopole antenna structure comprises a solid wire monopole antenna structure.

9. An IMD telemetry device according to claim 1, further comprising a display element, wherein:
   said electrically conducting structure comprises a casting for said display element, said casting having a perimeter; and
   said folded monopole antenna structure is routed around said perimeter of said casting.

10. An IMD telemetry device according to claim 9, wherein said folded monopole antenna structure is routed around a corner of said casting.

11. A radio frequency ("RF") antenna for an implanted medical device ("IMD") telemetry device having electrically conducting structures, said antenna comprising a conformal radiating element shaped to account for surface current cancellation caused by induced surface current on the electrically conducting structures, wherein said conformal radiating element comprises a planar inverted F-shaped structure having an input section, a first radiating section coupled to said input section, a second radiating section parallel to said first radiating section, and a bend section coupling said first radiating section to said second radiating section, said electrically conducting structure being located closer to said first radiating section than to said second radiating section.

12. An RF antenna according to claim 11, further comprising an RF connector coupled to said conformal radiating element, said RF connector being configured to establish RF coupling with an IMD signal transceiver.

13. An RF antenna according to claim 11, wherein said conformal radiating element is formed on an adhesive tape.

14. An RF antenna according to claim 11, wherein the operating frequency band of said RF antenna is approximately 401-405 MHz.

15. An implanted medical device ("IMD") telemetry device comprising:
   an electrically conducting structure;
   an antenna located proximate to said electrically conducting structure, and shaped to be anti-parallel with features of said electrically conducting structure; and
   a receiver coupled to said antenna, said receiver being configured to receive IMD signals via said antenna, said antenna being configured to account for surface current cancellation caused by induced surface current on said electrically conducting structure.

16. An implanted medical device ("IMD") telemetry device comprising:
   an electrically conducting structure;
   an antenna located proximate to said electrically conducting structure;
   an RF protection diode coupled to said antenna; and
   a receiver coupled to said antenna, said receiver being configured to receive IMD signals via said antenna, said antenna being configured to account for surface current cancellation caused by induced surface current on said electrically conducting structure.

17. An implanted medical device ("IMD") telemetry device comprising:
   a housing;
   an electrically conducting structure contained in said housing;
   a first antenna contained in said housing;
   a second antenna contained in said housing; and
   a transceiver coupled to said first antenna and coupled to said second antenna, said transceiver being configured to convey IMD signals via at least one of said first antenna and said second antenna, said first antenna and said second antenna each being configured to account for surface current cancellation caused by induced surface current on said electrically conducting structure;
   wherein at least one of said first antenna and said second antenna is shaped to be anti-parallel with features of said electrically conductive structure.

18. A radio frequency ("RF") antenna for an implanted medical device ("IMD") telemetry device having electrically conducting structures, said antenna comprising a conformal radiating element shaped to account for surface current cancellation caused by induced surface current on the electrically conducting structures, wherein said conformal radiating element is shaped to be anti-parallel with features of the electrically conductive structure.

19. A radio frequency ("RF") antenna for an implanted medical device ("IMD") telemetry device having electrically conducting structures, said antenna comprising:
   a conformal radiating element shaped to account for surface current cancellation caused by induced surface current on the electrically conducting structures; and
   an RF protection diode coupled to said conformal radiating element, said RF protection diode being configured to limit RF energy received by said RF antenna.

20. An RF antenna according to claim 19, wherein said RF protection diode is coupled between said conformal radiating element and an RF ground potential.

* * * * *

UNITED STATES PATENT AND TRADEMARK OFFICE
CERTIFICATE OF CORRECTION

PATENT NO. : 7,363,087 B2
APPLICATION NO. : 11/118306
DATED : April 22, 2008
INVENTOR(S) : David Nghiem et al.

It is certified that error appears in the above-identified patent and that said Letters Patent is hereby corrected as shown below:

Col. 12, line 22, delete "wire monople antenna structure" and insert in place thereof --wire structure--.

Signed and Sealed this

Seventeenth Day of February, 2009

JOHN DOLL
*Acting Director of the United States Patent and Trademark Office*